United States Patent [19]

Nakashima et al.

[11] Patent Number: 5,378,612

[45] Date of Patent: Jan. 3, 1995

[54] CULTURE MEDIUM FOR PRODUCTION OF RECOMBINANT PROTEIN

[75] Inventors: Kazuyuki Nakashima; Izumi Mimaki; Takayoshi Hamamoto, all of Kumamoto; Kenichi Masuda, Tokyo, all of Japan

[73] Assignees: Juridical Foundation The Chemo-Sero-Therapeutic Research Institute, Kumamot; Teijin Limited, Osaku, both of Japan

[21] Appl. No.: 997,670

[22] Filed: Dec. 28, 1992

Related U.S. Application Data

[63] Continuation of Ser. No. 696,567, May 8, 1991, abandoned.

[30] Foreign Application Priority Data

May 11, 1990 [JP] Japan ................... 2-121729
Apr. 15, 1991 [JP] Japan ................... 3-082269

[51] Int. Cl.$^6$ ................... C12P 21/02; C12N 5/02
[52] U.S. Cl. ................... 435/69.6; 435/240.31
[58] Field of Search ............. 435/240.1, 240.2, 240.31, 435/69.6

[56] References Cited

U.S. PATENT DOCUMENTS

| | | | |
|---|---|---|---|
| 4,216,203 | 8/1980 | Johnston | 435/70.5 |
| 4,533,637 | 8/1985 | Yamane et al. | 435/240.1 |

FOREIGN PATENT DOCUMENTS

| | | | |
|---|---|---|---|
| 57-74093 | 5/1982 | Japan | C12P 21/00 |
| 63-21469 | 12/1986 | Japan | C12N 5/00 |
| 63-18465 | 4/1988 | Japan | C12N 5/00 |
| 63-141584 | 6/1988 | Japan | C12N 5/00 |
| 63-279786 | 11/1988 | Japan | C12N 5/00 |
| 63-503273 | 12/1988 | Japan | C12N 5/00 |
| 25890 | 1/1990 | Japan | C12P 21/02 |
| 387173 | 4/1991 | Japan | C12N 5/00 |
| WO8705626 | 9/1987 | WIPO | C12N 1/38 |
| WO8901027 | 2/1989 | WIPO | C12N 5/00 |
| WO8906686 | 7/1989 | WIPO | C12N 5/02 |
| WO9003429 | 4/1990 | WIPO | C12N 5/00 |

OTHER PUBLICATIONS

D. Barnes, G. H. Sato, Cell, vol. 22, pp. 649–656 (1980).
The 8th symposium of the industrial basal technology for the next generation, preliminary report in biotechnology.
Pavirani, A. et al., Biotechnology, vol. 5, pp. 389–392 (1987).
Kaufman, R. J. et al., Mol. Cell. Biol., vol. 9, pp. 1233–1242 (1989).
Dorner, A. J. et al., Biol. Chem., vol. 254, pp. 20602–20607 (1989).
K. Tsuneoka, M. Shikita, J. Cell. Physiol., vol. 125, pp. 436–442 (1985).
T. Matsuhisa et al., Exp. Cell. Res., vol. 180, pp. 1–12 (1989).
K. Okabayashi et al., Cell Structure and Function, vol. 14, pp. 579–586 (1989).
Gauwerkry et al., *Brit. J. Haematol.* vol. 51, 1982, pp. 431–438.

Primary Examiner—Richard A. Schwartz
Assistant Examiner—James Ketter
Attorney, Agent, or Firm—Wegner, Cantor, Mueller & Player

[57] ABSTRACT

A culture medium without or with a low level of protein for culturing a transformed animal cell capable of continuously producing a protein prepared by using a genetic engineering technique, which contains a nonionic surfactant and cyclodextrin, and a method for producing a protein which comprises culturing a transformed animal cell capable of producing the desired protein prepared by using a genetic engineering technique in the culture medium.

11 Claims, No Drawings

CULTURE MEDIUM FOR PRODUCTION OF RECOMBINANT PROTEIN

This application is a continuation of U.S. application Ser. No. 07/696,567 filed May 8, 1991, now abandoned.

The present invention relates to a culture medium without or with low level of protein for culturing a transformed animal cell capable of continuously producing a protein prepared by using a genetic engineering technique and to a method for producing a useful protein which comprises culturing a transformed animal cell capable of producing said protein in said culture medium optionally supplemented with butyric acid or a salt thereof or another reagent for enhancing the production efficiency.

More particularly, the present invention relates to a culture medium without or with low level of protein for culturing a transformed animal cell capable of producing a recombinant coagulation Factor VIII and a method for producing a coagulation Factor VIII which comprises culturing a transformed animal cell capable of producing the recombinant coagulation Factor VIII in said culture medium optionally supplemented with butyric acid or a salt thereof or another reagent for enhancing the production efficiency of the Factor VIII. The culture medium of the present invention contains substantially no serum or plasma protein.

TECHNICAL BACKGROUND AND PRIOR ART

Nowadays, a recombinant engineering technique has been used for producing a variety of physiologically active substances as a recombinant protein in many kinds of host cells including an animal cell and a procaryotic cell such as E. coli. The animal cell is selected as a host cell in case that the protein produced after translation must be subjected to a modification procedure such as glycosilation or a construction of a hyperstructure so that the protein exhibits a physiological activity. However, in order to obtain a large amount of the physiologically active substance which is secreted in a culture supernatant of animal cell, several problems must be overcome. One is of the culture medium for culturing an animal cell capable of continuously producing a desired protein. Another is of the production efficiency of the desired protein in a culture medium in the production thereof by an animal cell.

In case of an animal cell culture, a culture medium must contain serum such as fetal calf serum (FCS). However, the serum including FCS is extremely expensive and besides it may possibly be contaminated with mycoplasma, virus and the like, and hence, it must be assayed for proving no contamination before use. In addition, it has not been easy to purify the desired substance from a culture supernatant since serum contains a variety of heterologous pertinacious substances. In this point of view, a serum-free culture medium has been developed including those supplemented with a protein whose property is well known such as insulin, transferrin, serum albumin and the like [D. Bames, G. H. Sato, Cell, 22 p649 (1980)].

However, it is more preferable not to use any protein. For such a purpose, it is also proposed to replace these proteins by other chemical compounds.

As an alternative of transferrin, an iron chelating agent such as ethylenediamine tetraacetate-iron complex or iron gluconate has been developed [Japanese Patent First Publication (Kokai) NO. 141584/1988; The 8th symposium of the industrial basal technology for the next generation, preliminary report in biotechnology]. As an alternative of serum albumin, a clathrate compound of α-cyclodextrin with an unsaturated fatty acid or a fat-soluble vitamin is known [Japanese Patent Second Publication (KoKoKu) No. 018465/1981]. It is also reported that an animal cell can be cultured without serum by adding a microemulsion of PLURONIC F-68 and a fat-soluble factor to a culture medium (PCT WO90/03429). However, the above-mentioned culture media without or with low level of protein are directed to merely cell growth and sometimes are not suitably applicable to the production of a recombinant protein. Therefore, there is a need for developing a culture medium which is capable of enhancing the production efficiency of recombinant protein.

As for the production efficiency of culture, in case of human coagulation Factor VIII, it is known that the Factor VIII is present in a starting plasma at a concentration of about 200 ng/ml but when a coagulation Factor VIII-producing cell prepared by the genetic engineering technique is cultured in a usual manner, only about 20 ng/ml of the product can be obtained from the culture supernatant [Pavirani, A. et al., Biotechnology 5, p. 389–392 (1987)]. Such a low level of production in case of the genetic engineering technique is assumed to be mostly due to a large molecular weight of the desired protein (about 300 KDa) and thereby difficulty of secretion of said protein from the host cell to the culture supernatant [Kaufman, R. J. et al., Mol. Cell Biol. 9, p1233–1242 (1989)].

As mentioned above, in case of culture of the Factor VIII-producing cell prepared by the genetic engineering technique, the production efficiency of the desired coagulation Factor VIII in the culture supernatant is quite low by the conventional culturing procedure. In this respect, for enhancing the production efficiency of the recombinant coagulation Factor VIII, an increase of cell density, an increase of stability of the produced protein and an enhancement of expression efficiency must be attained.

The present inventors have been investigated a culture medium which is effective for a large scale production of the recombinant coagulation Factor VIII protein by an animal cell. The present inventors have already found that the production efficiency of the recombinant protein with very low stability such as the coagulation Factor VIII can be improved by adding 1% serum albumin to the culture medium (Japanese Patent Application No. 157570/1988). This is assumed to be due to an effect of the serum albumin to stabilize the produced protein. However, the addition of pertinacious substance such as serum albumin makes it quite difficult to purify the desired production. Besides, since serum albumin is precious and expensive, it is substantially hard to use serum albumin as a culture component in large scale production.

In order to overcome the above-mentioned problem, a number of methods have recently been reported to enhance the production efficiency of the desired protein by adding a kind of additives to a cell culture system. Such known methods include, for example, a method in which the production efficiency of the desired protein is enhanced by adding an alkane acid (the most preferable is butyric acid) or a salt thereof to a culture system of protein-producing cell [Japanese Patent First Publication (Kohyo) No. 503273/1988] and a method in which butyric acid or a salt thereof is added to a beads culture system of protein-producing cell to enhance the production efficiency (PCT WO89/06686). There have also been reported a method for culturing an interferon-producing cell in which a cell capable of intrinsically producing interferon is cultured in a culture medium containing a straight chain alkane acid having 2 to 5 carbon atoms, preferably butyric acid, or a salt thereof prior to induction of interferon production (USP 4,216,203) and a method for enhancing an interferon production which comprises adding glucocorticoid, butyric acid or dimethylsulfoxide to a culture medium [Japanese Patent First Publication (Kokai) No. 74093/1982] and the like.

The above-mentioned conventional methods are directed to enhancement of the production efficiency by adding a straight chain alkane acid, most preferably butyric acid, to a culture system for production of useful protein and in fact the production efficiency of protein is enhanced by these methods through addition of such additives. However, in case of a certain combination of a desired protein and a producing cell, the production efficiency is quite low even when the alkane acid is added to a culture medium and a single addition of butyric acid is even more insufficient. A typical example of such insufficiency is the production of coagulation Factor VIII by utilizing the genetic engineering technique.

Actually, it is reported that, when a recombinant animal cell capable of producing the coagulation Factor VIII prepared by using the genetic engineering technique is cultured to produce a desired protein, the addition of a butyrate (in this case, sodium butyrate) to the culture medium increases an amount of said coagulation Factor VIII produced in the culture supernatant by about 1.3 to 2.5 times as compared to the culture medium with no addition of the butyrate [Dorner, A. J. et al., J. Biol. Chem. 254, p20602–20607 (1989)]. However, the enhancement of production efficiency is still insufficient even by the addition of the butyrate in case of a production system having originally low production efficiency such as the production system of the coagulation Factor VIII, and still more enhancement of the production efficiency is required for the production of coagulation Factor VIII on industrial scale.

BRIEF SUMMARY OF THE INVENTION

Under such circumstances, the present inventors have studied intensively to develop a culture medium without or with low level of protein having a sufficiently high production efficiency of a desired protein, and as a result, have found that a culture medium without or with low level of protein capable of enhancing the growth rate and the production efficiency of the recombinant protein can be obtained without using serum albumin by adding dimethyl-$\alpha$-cyclodextrin and a nonionic surfactant such as ethyleneoxide polypropyleneglycol (PLURONIC F-68), polyoxyethylene sorbitan monolaurate (Tween 20), polyoxyethylene sorbitan monooleate (Tween 80) and the like to a culture medium of a transformed cell capable of producing the recombinant coagulation Factor VIII. The present inventors have also found that the culture medium of the present invention provides far more excellent effect of enhancing the production efficiency of the recombinant protein than the conventional culture medium in which butyric acid or a salt thereof is solely added.

An object of the present invention is to provide a culture medium without or with low level of protein for culturing a transformed animal cell capable of continuously producing a protein prepared by using a genetic engineering technique, which contains a nonionic surfactant and cyclodextrin.

Another object of the present invention is to provide the culture medium as mentioned above which additionally contains butyric acid or a salt thereof and a lithium salt.

Still another object of the present invention is to provide a method for producing a protein which comprises culturing a transformed animal cell capable of producing said desired protein prepared by using a genetic engineering technique in the culture medium as mentioned above.

These and other objects and advantages thereof of the invention will be apparent to those skilled in the art from the following description.

DETAILED EXPLANATION OF THE INVENTION

In the present invention, the term "production efficiency" is shown by an efficiency in increase of concentration of the product in a culture supernatant and the term "expression efficiency" means an ability of a transformed cell to express the product.

In culture of a transformed cell capable of continuously producing a desired protein prepared by using the genetic engineering technique, a culture medium of the present invention containing a nonionic surfactant and $\alpha$-cyclodextrin (hereinafter referred to as "$\alpha$-CD") can be used as an alternative of the conventional serum albumincontaining culture medium. The culture medium of the present invention for producing a useful protein may further contain butyric acid or a salt thereof and another reagent for synergistically enhancing the production efficiency such as a lithium salt or a lipopolysaccharide (hereinafter referred to as "LPS").

The culture medium of the present invention containing a nonionic surfactant and $\alpha$-cyclodextrin is used for culturing a transformed cell capable of continuously producing a desired protein prepared by using the genetic engineering technique to provide a higher production efficiency which is twice or more higher than the culture medium containing no additives and equal to the culture medium containing serum albumin.

The nonionic surfactant used in the culture medium of the present invention includes, for example, PLURONIC surfactants such as PLURONIC F-61, PLURONIC F-68, PLURONIC F-71, PLURONIC F-108 and the like; and sorbitan surfactants such as polyoxyethylene sorbitan monolaurate (Tween 20), polyoxyethylene sorbitan monocleate (Tween 80) and the like.

The cyclodextrin is preferably an unmodified cyclodextrin, $\alpha$-cyclodextrin (hereinafter referred to as "$\alpha$-CD"), more preferably, 2,6-dimethyl-$\alpha$-cyclodextrin (hereinafter referred to as "DM-$\alpha$-CD"). The DM-$\alpha$-CD used herein means a cyclodextrin consisting of 6 glucose units wherein 2- and 6-hydroxy groups on the glucose residue is methylated.

A concentration of each additives used in the culture medium of the present invention should be in such a range that does not adversely affect on the growth of the transformed cell and the production efficiency. Suitable culture medium of the present invention contains 0.005 to 1.0% (% by weight, hereinafter the same), preferably 0.01 to 0.1%, of the PLURONIC surfactant and 0.001 to 0.3%, preferably 0.01 to 0.1%, of the $\alpha$-CD (more preferably DM-$\alpha$-CD). Other suitable culture medium contains 0.001 to 0.006%, preferably 0.002 to 0.003%, of the sorbitan surfactant and 0.001 to 0.3%, preferably 0.01to 0.1%, of α-CD (more preferably DM-α-CD).

The culture medium of the present invention containing the nonionic surfactant and the cyclodextrin is used for culture in the following manner. That is, a desired cell can be multiplied by firstly culturing the cell in a culture medium with 10% serum for 8 to 24 hours and then keeping the culture with substitution of the culture medium with a culture medium containing the additives of the present invention at a suitable concentration. The additives-containing culture medium should be sterilized. In one embodiment, the nonionic surfactant and the cyclodextrin are firstly added to a basal culture medium and the culture medium is then subjected to filtration sterilization. Alternatively, a solution containing a high concentration of the nonionic surfactant and the cyclodextrin is steam-sterilized and then a suitable amount of the sterilized nonionic surfactant and cyclodextrin is added to a sterilized basal culture medium.

The basal culture medium to be added with the additives includes conventional media, for example, ASF medium (manufactured by Ajinomoto K. K.). There may also be used any other synthetic culture media containing insulin, transferrin, ethanolamine, selenite, etc.

The culture medium without or with low level of protein of the present invention may further contain butyric acid or a salt thereof and another reagent capable of enhancing the effect of these additives when the culture medium of the present invention is used for culturing an animal cell capable of continuously producing a desired protein in the conventional manner. Although this type of the culture medium of the present invention may be used for any desired protein or any kind of cells, it can most advantageously be used for culturing a transformed cell capable of producing coagulation Factor VIII.

Butyric acid used as a reagent for enhancing the expression efficiency of the desired protein is usually used in the form of a salt, particularly as sodium salt, but any other salts may be used, and a free acid may also be used. The lithium salt used as another reagent for synergistically enhancing the effect of butyric acid or salt thereof may be of any kind of salts but is preferably selected from lithium chloride, lithium acetate, and the like. Besides, any kind of the LPS derived from any origin may be used.

These additives may be added to the culture medium of the present invention in such an amount that enhances the production efficiency of the desired protein but does not substantially adversely affect on the growth rate of the cultured cell. The butyric acid or salt thereof is suitably used at a concentration of 0.1 to 5.0 mM, preferably 0.5 to 2.0 mM and the lithium salt is used at a concentration of 2.0 to 50 mM, preferably 10 to 50 mM. The LPS is suitably used at a concentration of 10 ng/ml to 1.0 mg/ml, preferably 0.5 to 100 µg/ml.

In case that the cell capable of producing the desired protein is an anchorage dependent cell, the cell is firstly adhered to a culture vessel by means of a culture medium containing an adherent protein such as serum or fibronectin and then grown in the culture medium without or with low level of protein of the present invention which contains the above-mentioned nonionic surfactant and the α-cyclodextrin in the basal medium. When the cell growth reaches at 80 to 90% confluence, the culture medium is replaced with the culture medium of the present invention which additionally contains butyric acid or salt thereof and the reagent capable of synergistically enhancing the effect of butyric acid or salt thereof, and thereby an excellent production efficiency can be obtained.

The produced protein can be collected and purified in the conventional manner. That is, the protein with a desired purification and concentration can be obtained by a known biochemical procedure including a precipitation, various chromatographic procedures, or a combination thereof. The additives of the present invention do not adversely affect on these procedures.

When the reagent for synergistically enhancing the effect of butyric acid or salt thereof is added to the culture medium without or with low level of protein of the present invention which contains the nonionic surfactant and the α-cyclodextrin, the production efficiency of the desired protein is increased by 4 times as compared to the basal medium with no additives and by more than twice as compared to the culture medium containing serum albumin.

The present invention is illustrated in more detail by the following Examples but should not be construed to be limited thereto.

EXAMPLE 1

(Determination of effective concentration of PLURONIC F-68)

A basal medium was ASF medium 104 (Ajinomoto K. K.) to which 0.1% DM-α-CD was added. To this medium was added PLURONIC F-68 (manufactured by GIBCO) at various concentrations. The cell to be cultured was a Chinese hamster ovary (CHO) cell capable of producing coagulation Factor VIII prepared by using a genetic engineering technique (Japanese Patent Application No. 85454/1988; this cell has been deposited at Fermentation Research Institute, Agency of Industrial Science and Technology, Japan, in deposition No. FERM P-9873, on Feb. 17, 1988, which was re-deposited at the same depositary under Budapest Treaty as FERM BP-2014 on Aug. 24, 1988). The cell was cultured on a culture dish (manufactured by Falcon). At this stage, the culture medium used for growing the cell was the ASF medium 104 containing 10% fetal calf serum (FCS) and the cell was inoculated at a cell density of $5 \times 10^5$ cells per well having the base area of 9.6 cm$^2$.

After sufficient growth of the cell, the culture medium was removed by suction and replaced with the basal media each containing PLURONIC F-68 at a fixed concentration. Each 3 ml per well of the culture medium was used and the cells were cultured in 5% CO$_2$ at 37° C. As a control, a culture medium with serum albumin containing no DM-α-CD was used for comparison. The serum albumin used was 20% human serum albumin preparations (manufactured by Chemo-Sero-Therapeutic Research Institute). The DM-α-CD was the product manufactured by Cosmobio Co. Ltd. A cell number was counted with a hemocytometer via microscopic observation as for live cells which Were not dyed with trypan blue (dead cells were dyed with trypan blue). The activity of coagulation Factor VIII was measured as an ability to decrease delay of partial thromboplastin time of coagulation Factor VIII-defective plasma in the standard blood coagulation quantitative analysis [Hardisty et al., Thrombosis et Diathesis Haemologica 72, p215 (1962)] wherein a standard plasma for quantification of coagulation factor (manufactured by Dade) was used as a standard, and the ability in said standard was counted as one unit (International Unit; IU)/ml. The results are shown in Table 1.

The results shown in Table 1 confirmed that the use of the surfactant such as PLURONIC F-68 at a concentration ranging from 0.005 to 1.0% in addition to 0.1% DM-α-CD enhanced the production efficiency of the recombinant coagulation Factor VIII.

TABLE 1

(Varying concentration of Pluronic F-68)

| Culture medium | Conc. of PLURONIC F-68 (%) | Conc. of Factor VIII (IU/ml) 24 h. | 48 h. | No. of live cells ($\times 10^6$/ml) |
|---|---|---|---|---|
| ASF medium 104 + 0.1% DM-α-CD | 0 | 1.1 | 1.9 | 0.67 |
| | 0.001 | 1.0 | 1.6 | 0.65 |
| | 0.005 | 1.7 | 2.6 | 0.66 |
| | 0.01 | 2.2 | 3.5 | 0.86 |
| | 0.1 | 2.5 | 3.8 | 0.91 |
| | 1.0 | 2.2 | 2.3 | 0.50 |
| | 3.0 | 0.6 | 1.0 | 0.38 |
| ASF medium 104 + 1% HSA | — | 2.0 | 3.2 | 0.70 |

EXAMPLE 2

(Determination of effective concentration of Tween-80)

The procedure of Example 1 was repeated except that Tween-80 was employed in place of PLURONIC F-68. The results are shown in Table 2.

The results shown in Table 2 confirmed that the use of Tween-80 at a concentration of 0.001 to 0.006% in addition to 0.1% DM-α-CD enhanced the production efficiency of the recombinant coagulation Factor VIII.

TABLE 2

(Varying concentration of Tween-80)

| Culture medium | Conc. of Tween-80 (%) | Conc. of Factor VIII (IU/ml) 24 h. |
|---|---|---|
| ASF medium 104 + 0.1% DM-α-CD | 0 | 1.1 |
| | 0.0005 | 1.0 |
| | 0.001 | 1.5 |
| | 0.002 | 2.6 |
| | 0.003 | 2.4 |
| | 0.006 | 1.6 |
| ASF medium 104 + 1% HSA | — | 2.5 |

EXAMPLE 3

(Determination of effective concentration of dimethyl-α-cyclodextrin)

The procedure of Example 1 was repeated except that the ASF medium 104 containing 0.1% PLURONIC F-68 was used and to this medium was added the DM-α-CD at various concentrations to determine the effect of the DM-α-CD while using the serum albumin-containing medium as a control. The results are shown in Table 3.

As a result, it was found that the DM-α-CD at a concentration of 0.001 to 0.3% in addition to 0.1% PLURONIC F-68 enhanced the production efficiency of the recombinant coagulation Factor VIII. NO enhancing effect was observed with the DM-α-CD at a concentration of less than 0.001% while a cytotoxic effect was shown at a concentration of more than 0.3%.

TABLE 3

(Varying concentration of DM-α-CD)

| Culture medium | Conc. of DM-α-CD (%) | Conc. of Factor VIII (IU/ml) 24 h. | 48 h. | No. of live cells ($\times 10^6$/ml) |
|---|---|---|---|---|
| ASF medium 104 + 0.1% PLURONIC F-68 | 0 | 1.3 | 2.4 | 0.58 |
| | 0.0005 | 1.2 | 2.3 | 0.55 |
| | 0.001 | 1.3 | 2.8 | 0.62 |
| | 0.01 | 2.4 | 4.4 | 0.76 |
| | 0.1 | 2.9 | 5.1 | 0.72 |
| | 0.3 | 3.2 | 4.8 | 0.33 |
| | 0.5 | 2.1 | 3.4 | 0.22 |
| ASF medium 104 + 1% HSA | — | 2.5 | 5.5 | 0.77 |

Reference Example 1

(Evaluation of another additives for enhancing the effect of butyric acid or salt thereof)

The culture medium was removed by suction and replaced with another culture medium which was prepared by adding various additives as shown in Table 4 to a medium comprising the ASF medium and butyric acid. The butyric acid was added as a sodium salt. Control culture solution did not contain butyric acid and other additives. Lithium acetate, lithium chloride, sodium acetate and hydroxyurea were products of a special grade manufactured by Wako Jun-yaku Kogyo K. K., cesium chloride was a product of a special grade manufactured by Nakarai Kagaku Yakuhin K. K., and lipopolysaccharide (LPS) and concanavalin A was a product of a special grade manufactured by Sigma Chemical.

The results are shown in Table 4. As a result, it was found that lithium acetate, lithium chloride or lipopolysaccharide (LPS) enhanced the effect of butyric acid by about 1.3 to 4.0 times. These additives at the concentration shown in Table 4 did not change the cell number significantly, and hence, was confirmed not to be substantially adversely effective on the growth of the cell.

TABLE 4

(Evaluation of additives for enhancing the effect of butyric acid or salt thereof)

| Culture medium | Additives | Conc. of Factor VIII (IU/ml) 24 h. | 48 h. |
|---|---|---|---|
| ASF medium 104 + 1 mM sodium butyrate | — | 38.8 | 94.3 |
| | 10 mM Lithium acetate | 40.0 | 126.1 |
| | 10 mM Lithium chloride | 45.4 | 123.6 |
| | 10 mM Sodium acetate | 33.2 | 99.0 |
| | 10 mM Cesium chloride | 9.5 | 12.6 |
| | 0.3 mM Hydroxyurea | 29.3 | 83.4 |
| | 1 μg/ml LPS | 88.1 | 389.2 |
| | 10 μg/ml Concanavalin A | 24.1 | 70.0 |
| ASF medium 104 | — | 11.9 | 12.6 |

Reference Example 2

(Enhancement of the effect of butyric acid or salt thereof with lithium acetate)

The procedure of Example 1 was repeated except that 1 mM butyric acid and lithium acetate at each concentration as shown in Table 5 were added to the ASF medium 104 and the culture was continued for 72 hours. The results are shown in Table 5. As a result, it was found that the effect of butyric acid was significantly enhanced with lithium acetate at a concentration ranging from 5.0 to 50 mM.

TABLE 5

(Varying concentration of lithium acetate)

| Culture medium | Conc. of Lithium acetate (mM) | Conc. of Factor VIII (IU/ml) 24 h. | 48 h. |
| --- | --- | --- | --- |
| ASF medium 104 + | 0 | 49.3 | 98.3 |
| 1 mM sodium butyrate | 5 | 68.4 | 131.1 |
|  | 10 | 67.8 | 127.3 |
|  | 20 | 68.2 | 123.1 |
|  | 50 | 50.5 | 110.9 |
| ASF medium 104 | — | 24.9 | 28.1 |

Reference Example 3

(Enhancement of the effect of butyric acid or salt thereof with lithium chloride)

The procedure of Example 1 was repeated except that 1 mM butyric acid and lithium chloride at each concentration as shown in Table 6 were added to the ASF medium 104 and the culture was continued for 72 hours. The results are shown in Table 6. As a result, it was found that the effect of butyric acid was significantly enhanced with lithium chloride at a concentration ranging from 5.0 to 50 mM.

TABLE 6

(Varying concentration of lithium chloride)

| Culture medium | Conc. of Lithium chloride (mM) | Conc. of Factor VIII (IU/ml) 24 h. | 48 h. |
| --- | --- | --- | --- |
| ASF medium 104 + | 0 | 49.5 | 92.1 |
| 1 mM sodium butyrate | 5 | 69.8 | 142.3 |
|  | 10 | 65.4 | 125.4 |
|  | 20 | 69.6 | 127.4 |
|  | 50 | 52.3 | 110.4 |
| ASF medium 104 | - | 24.9 | 28.1 |

EXAMPLE 4

(Evaluation of the effect of a butyrate and a lithium salt)

To a basal medium (ASF medium 104) were added 0.1% DM-α-CD and 0.1% PLURONIC F-68 to prepared a culture medium (medium A). Then, to the medium A were further added 1 mM sodium butyrate and 5 mM lithium acetate to prepare a culture medium (culture medium B). Using these culture media, the procedure of Example 1 was repeated except that the culture was continued for 48 hours. The results are shown in Table 7.

TABLE 7

(Evaluation of the effect of a butyrate and a lithium salt)

| Culture medium | Conc. of Factor VIII (IU/Mi) 24 h. | 48 h. |
| --- | --- | --- |
| ASF medium 104 + 0.1% PLURONIC F-68 + 0.1% DM-α-CD | 2.9 | 3.8 |
| ASF medium 104 + 0.1% PLURONIC F-68 + 0.1% DM-α-CD + 1 mM sodium butyrate + 5 mm lithium acetate | 5.7 | 8.0 |
| ASF medium 104 | 1.4 | 1.9 |
| ASF medium 104 + 1% HSA | 2.6 | 3.1 |

What is claimed is:

1. A method for producing coagulation Factor VIII which comprises culturing a Chinese Hamster Ovary cell which produces said coagulation Factor VIII, in a culture medium comprising a nonionic surfactant and a cyclodextrin and collecting the secreted coagulation Factor VIII from the culture medium, wherein the nonionic surfactant is selected from the group consisting of a pluronic surfactant and a sorbitan surfactant.

2. The method of claim 1 wherein the surfactant is PLURONIC F-68.

3. The method of claim 1 wherein the nonionic surfactant and cyclodextrin are each present at a concentration of from 0.005 to 1.0% and 0.001 to 0.3%, respectively.

4. A method for producing coagulation Factor VIII which comprises culturing a Chinese Hamster Ovary cell which produces said coagulation Factor VIII, in a culture medium comprising a nonionic surfactant selected from the group consisting of a PLURONIC surfactant and a sorbitan surfactant, and a cyclodextrin and collecting the secreted coagulation Factor VIII from the culture medium, wherein the cyclodextrin is selected from the group consisting of unmodified α-cyclodextrin and methylated α-cyclodextrin.

5. A method for producing coagulation Factor VIII which comprises culturing transformed Chinese Hamster Ovary cell which produces said coagulation Factor VIII, in a culture medium comprising a nonionic surfactant selected from the group consisting of a PLVRONIC surfactant and a sorbitan surfactant, butyric acid or a salt thereof in a concentration of from 0.1 to 5.0 mM, a lithium salt in a concentration of from 2.0 to 50 mM, and a cyclodextrin, and collecting the secreted coagulation Factor VIII from the culture medium.

6. A culture medium, optionally containing a low level of protein, for culturing a transformed Chinese Hamster Ovary Cell which produces coagulation Factor VIII, which comprises a nonionic surfactant selected from the group consisting of a PLURONIC surfactant and a sorbitan surfactant and a cyclodextrin in admixture with a conventional culture medium.

7. The culture medium of claim. 6 wherein the nonionic surfactant is a PLURONIC surfactant selected from the group consisting of PLURONIC F-61, PLURONIC F-68, PLURONIC F-71 and PLURONIC F-108 or a sorbitan surfactant selected from the group consisting of polyoxyethylene sorbitan monolaurate and polyoxyethylene sorbitan monooleate.

8. The culture medium of claim 6 wherein the cyclodextrin is a member selected from the group consisting of unmodified α-cyclodextrin and methylated α-cyclodextrin.

9. The culture medium of claim 6 wherein the PLURONIC surfactant and the cyclodextrin are each contained at a concentration of 0.005 to 1.0%, and 0.001 to 0.3%, respectively.

10. The culture medium of claim 6 wherein the sorbitan surfactant and the cyclodextrin are each contained at a concentration of 0.001 to 0.006%, and 0.001 to 0.3%, respectively.

11. The culture medium of any of claims 6 to 10 which additionally contains butyric acid or a salt thereof and a lithium salt at a concentration of 0.1 to 5.0 mM and 2.0 to 50 mM, respectively.

* * * * *